United States Patent [19]

Ninomiya et al.

[11] Patent Number: 5,220,169

[45] Date of Patent: Jun. 15, 1993

[54] SURFACE ANALYZING METHOD AND APPARATUS

[75] Inventors: Ken Ninomiya, Higashimatsuyama; Keizo Suzuki, Kodaira; Shigeru Nishimatsu, Kokubunji, all of Japan

[73] Assignee: Hitachi, Ltd., Tokyo, Japan

[21] Appl. No.: 517,692

[22] Filed: May 2, 1990

[30] Foreign Application Priority Data

Sep. 1, 1989 [JP] Japan .................... 1-224462

[51] Int. Cl.⁵ .................... G01N 23/00; G21K 5/00
[52] U.S. Cl. .................... 250/358.1; 378/206; 250/359.1; 250/458.1; 250/459.1; 250/461.1
[58] Field of Search .................... 378/206; 250/358.1, 250/360.1, 372, 458.1, 459.1, 461.1, 491.1, 359.1

[56] References Cited

U.S. PATENT DOCUMENTS

| | | | |
|---|---|---|---|
| 4,521,905 | 6/1985 | Hosokawa | 378/206 |
| 4,844,617 | 7/1989 | Kelderman et al. | 250/372 |
| 4,969,177 | 11/1990 | Otsuki et al. | 378/206 |

FOREIGN PATENT DOCUMENTS

| | | | |
|---|---|---|---|
| 1021814 | 2/1953 | France | 378/206 |
| 6188200 | 10/1984 | Japan. | |
| 62-26556 | 11/1987 | Japan. | |
| 1-201200 | 10/1989 | Japan | 378/206 |

OTHER PUBLICATIONS

'X-Ray Tri-Scope' Flier, Sep. 1949.

Primary Examiner—Constantine Hannaher
Assistant Examiner—Edward J. Glick
Attorney, Agent, or Firm—Fay, Sharpe, Beall, Fagan, Minnich & McKee

[57] ABSTRACT

A first beam of light having a wavelength ranging from a soft X-ray to a vacuum ultraviolet region is focused into a thin beam of light and irradiated upon a surface of a specimen, and physical information obtained as a result of such irradiation is detected to obtain information of the surface of the specimen. A second beam of light is focused into a thin beam of light and irradiated at the irradiation spot of the first beam of light upon the surface of the specimen, and the position of the irradiation spot of the second beam of light on the surface of the specimen is visually observed to located the position of the irradiation point of the first beam of light on the surface of the specimen.

40 Claims, 8 Drawing Sheets

SURFACE ANALYZING METHOD AND APPARATUS

BACKGROUND OF THE INVENTION

This invention relates to surface analyzing technology for a small area, and more particularly to a surface analyzing method and apparatus by which an area for the analysis is set and located readily.

In recent years, the importance of surface analyzing technology for a small area has been and is increasing. For example, in analysis and identification of residual contaminants on a surface of a semiconductor circuit element, a small area having a diameter of several microns to 0.1 micron or so is an object for the analysis. Further, also in analysis of formation of a film on a surface or of a chemical reaction such as a catalytic reaction, an area of diameter smaller than 0.1 micron is an object for the analysis.

For such demands, conventionally a method has been proposed wherein an X-ray beam is focused and irradiated upon a small area of a surface of a specimen and a fluorescent X-ray radiated from the surface of the specimen is observed (refer to, for example, Japanese Patent Laid-Open No. 62-265556 and Japanese Patent Laid-Open No. 61-88200).

With the prior art described above, however, no attention is paid to means for setting the X-ray beam with a high degree of accuracy in an area of a surface of a specimen that should be analyzed nor to means for precisely locating which area is being analyzed. In the case where the magnitude of an area to be analyzed is on the order of microns or less, it is difficult to conduct a reliable surface analysis without suitable means for setting and locating an area for the analysis.

SUMMARY OF THE INVENTION

Accordingly, it is an object of the present invention to provide a surface analyzing method and apparatus for a small area by which the setting and locating of an area for the analysis can be effected readily.

In order to attain the object, according to the present invention, a plurality of beams of light are focused and irradiated upon a surface of a specimen. At least one of the plurality of the beams of light is a beam of light for the analysis, and the beam or beams of light for the analysis are beams of light each having a wavelength ranging from a soft X-ray to a vacuum ultraviolet region and are each monochromatic light. Such light for the analysis is focused and irradiated upon a small area of a surface of a specimen using a reflecting type optical element. The irradiation area of the light is a so-called analysis area in small area surface analysis. A surface analysis is effected by surveying particles such as electrons, photons, ions and neutral particles emitted from the surface of the specimen as a result of irradiation of the light for the analysis. Particularly, an electron spectroscopy which analyzes energy of emitted electrons is useful for the analysis of a chemical state of the surface of the specimen.

The beam or beams of light other than the beam or beams of light which are used for such surface analysis are used for the setting and locating of an area for the analysis. Each of the beam or beams of light for the setting and locating of an area for the analysis is focused and irradiated such that the center of an irradiated spot on the surface of the specimen may coincide with the center of an irradiated spot of each of the beam or beams of light for the surface analysis on the surface of the specimen. An optical element for such focusing may be the same as or different from an optical element for the focusing of the beam or beams of light for the surface analysis. Focused spots of the beams of light for the setting and locating of an area for the analysis on or near the surface of the specimen are observed using an enlarging surveying means to effect setting and locating of an area for the analysis.

Operation of the characteristic construction described above according to the present invention is such as follows. First, surface analyzing means for a small area and its operation will be described. From a surface of a specimen upon which light of a wavelength ranging from a soft X-ray to a vacuum ultraviolet region irradiates, electrons, photons, ions, neutral particles and so forth are emitted. Accordingly, elements and a chemical state of the irradiated area can be identified by analyzing energy and kinds of those particles.

By the way, in order to focus a beam of light of a wavelength ranging from a soft X-ray to a vacuum ultraviolet region upon an area having a diameter smaller than several microns, a focusing optical element having a very small aberration is required. Such optical element cannot be realized with a single reflecting mirror, but can be realized with a combination of aspherical reflecting mirrors such as Walter type mirrors or Kirkpatric-Betz type mirrors. Thus, light of a wavelength ranging from a soft X-ray to a vacuum ultraviolet region can be focused onto a very small area having a diameter smaller than several microns to 1 micron using any of such reflecting mirrors.

A reflecting type optical element has no chromatic aberration (difference in focusing characteristic between lights having different wavelengths). In surface analysis, the wavelength of light to be irradiated upon a surface of a specimen is changed frequently in order to change a surface sensitivity or the like. In this instance, where an optical element of the reflecting type is employed, the position or the size of an area for the analysis is not changed basically by a change in wavelength of irradiated light because there is no chromatic aberration. This characteristic is essential for small area analysis.

As described above, a surface analysis of a small area can be conducted by focusing and irradiating light of a wavelength ranging from a soft X-ray to a vacuum ultraviolet region upon a surface of a specimen using a reflecting type optical element and surveying particles radiated from the surface of the specimen.

Subsequently, means for setting and locating an area for the analysis and operation thereof will be described. As described hereinabove, light focused upon a surface of a specimen is used also for the setting and locating of an area for the analysis. An optical element for use for the focusing may be the same reflecting type optical element as the optical element used for the focusing of light for the surface analysis or may be a different optical element. Particularly in the former case, there is an advantage that the apparatus system is simplified. Since a reflecting type optical element has no chromatic aberration, the optical element for the focusing of light for the surface analysis can be used as it is also as an optical element for the focusing of light for the setting and locating of an area for the analysis.

Preferably, a spot of light (diameter of a beam) focused on a surface of a specimen for the setting and locating of an area for the analysis has a diameter substantially similar to that of the area for the analysis, that is, a diameter on the order of several microns to 0.1 micron. To this end, light for the setting and grasping of an area for the analysis must be a visible radiation or light having a smaller wavelength than a visible radiation such as, for example, an ultraviolet radiation. Those radiations can be focused readily upon a small area having a diameter from several microns to 1 micron or less using a low aberration optical element. Particularly where visible radiation is used, a spot of focused light can be visually observed directly. Meanwhile, even where light such as ultraviolet radiation having a wavelength shorter than that of visible radiation is used, a spot of focused light can be visually observed using a fluorescent screen or the like. Accordingly, if the center of a beam of light for the setting and locating of an area for the analysis on a surface of a specimen is made to coincide with the center of another beam of light for the surface analysis on the surface of the specimen, then the setting and locating of the area for the analysis can be effected readily by visual observation using an enlarging surveying means such as, for example, an optical microscope. While a light source of a beam of light for the setting and locating of an area for the analysis can be selected arbitrarily, preferably a laser source is employed taking the brightness and the facility of handling into consideration.

It is to be noted that the following method may be employed for the setting and grasping of an area for the analysis. In particular, in addition to a beam of light for the surface analysis, light having a wavelength ranging from a soft X-ray region to a vacuum ultraviolet region is irradiated simultaneously as a beam of light for the setting and locating of an area for the analysis over an area including and wider than an irradiation spot of the beam of light for the surface analysis (in short, an area for the analysis). As a result of such irradiation of the light, fluorescent light is produced from the irradiation area in addition to electrons. It is well known that, when light of a wavelength ranging from a soft X-ray to a vacuum ultraviolet region is irradiated, fluorescent light and so forth are produced. If such fluorescent light is detected using an enlarging optical system, then an enlarged image of the irradiation area can be obtained.

Also in the irradiation area of the beam of light for the surface analysis, fluorescent light is produced in addition to emission of electrons described above. Accordingly, since the irradiation area of the beam of light for the surface analysis on the enlarged image is observed as a spot brighter than a location around the spot, locating of the area for the analysis can be effected readily making use of the fact. Locating of the area for the analysis can be effected more in detail by changing the focusing or the magnification of the optical system for the production of fluorescent light or the enlarging optical system.

A beam of light for the analysis of a small area may have different energy from that of a beam of light for the production of fluorescent light. The point of the method is that a plurality of beams of light are used and are optically processed such that at least one of irradiation areas of the beams of light (an area for the analysis) may be included in the other light beam irradiation area or areas (area or areas for the observation of an enlarged image) in order to facilitate locating of the area for the analysis. Here, simultaneous radiation of the beams of light is required when locating of the area for the analysis is to be confirmed. However, a beam or beams of light for the production of fluorescent light are not necessarily required when a small area is to be analyzed after such confirmation of the area for the analysis.

BRIEF DESCRIPTION OF THE DRAWINGS

FIG. 4 shows another embodiment.

DESCRIPTION OF THE PREFERRED EMBODIMENTS

Several preferred embodiments of the present invention will be described below with reference to the accompanying drawings.

Figure 1:
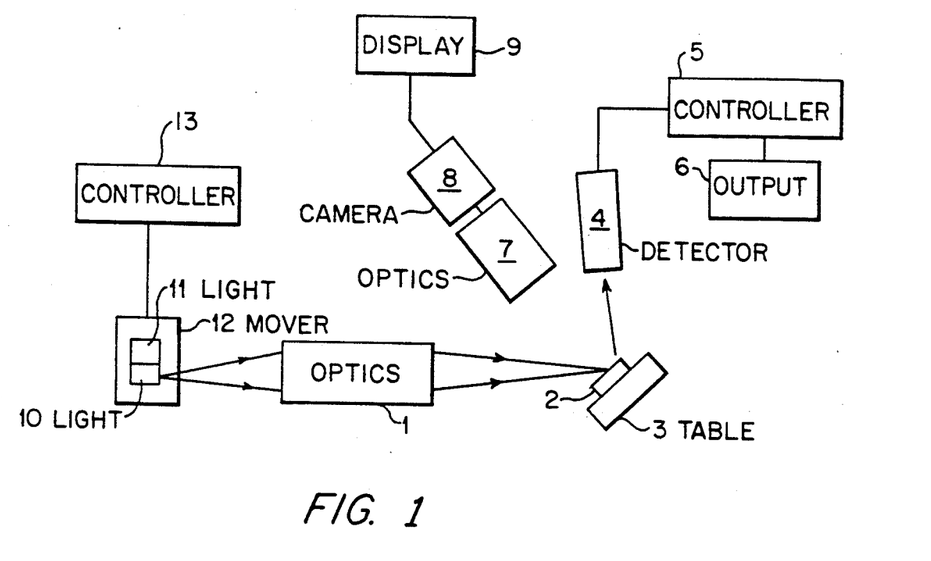
FIG. 1 shows the general construction of a surface analyzing apparatus according to an embodiment of the present invention.

Embodiment 1:

Referring to FIG. 1, the surface analyzing apparatus shown includes a light source 10 for the setting and locating of an area for the analysis (hereinafter referred to as area locating light source) and another light source 11 for the analysis of a surface which emits a soft X-ray or light in a vacuum ultraviolet region (hereinafter referred to as surface analyzing light source). (Where a spectrometer is used in combination with a light source, an exit slit of the spectrometer becomes the light source 11 in FIG. 1. This also applies to description of any embodiment described hereinbelow.) In the present embodiment, a visible radiation is used for the setting and locating of an area for the analysis, and the light source 10 for the same may be, for example, a laser source. A He-Ne laser is commonly employed as a laser source. Light from the area locating light source 10 is focused upon a surface of a specimen 2 using an optical system 1, i.e. optics. The optical system 1 is constructed using a reflecting type optical main component. An enlarged image of the surface of the specimen 2 and a visible radiation image of a spot of focused light produced on the surface of the specimen 2 are produced by an optical system 7 for the enlarging of an image such as, for example, an optical microscope and a camera 8 connected to the optical system 7, and the enlarged images are projected on an image screen of a display unit 9. Thus, an operator finely adjusts, while observing the projected images, the position of a specimen table 3 on which the specimen 2 is placed so that the spot of the focused light may coincide with an area on the surface of the specimen 2 to be analyzed. Consequently, an area for the analysis is set.

Subsequently, when a surface analysis is to be performed, the surface analyzing light source 11 is moved to the position at which the area locating light source 10 was precedently located upon setting of the area for the analysis described above. Such movement is performed using a moving mechanism 12 under the control of a controller 13. The moving mechanism 12 is capable of providing precision movement of the surface analyzing light source 11 on the order of microns. Since the optical system 1 consisting of a reflecting type optical element has no chromatic aberration, light from the surface analyzing light source 11 is also focused upon the position on the surface of the specimen 2 (area for the analysis) set and confirmed on the image screen of the display unit 9. Particles such as electrons, photons, ions and neutral particles emitted from the surface of the specimen 2 as a result of such irradiation of the light for the surface analysis are detected by a detector 4. Here, if an energy analyzing function is required for such detection, then an energy analyzing type detector should be used as the detector 4. The detector 4 is controlled by a controller 5. A particle detection signal from the detector 4 is once processed by the controller 5 and then outputted to an outputting/displaying device 6.

With the surface analyzing apparatus of the present embodiment, setting and grasping of an area for the analysis can be effected with a tolerance on the order of microns or less by focusing and irradiating light from the area locating light source 10 upon a surface of the specimen and observing the position of a spot of the focused light on the surface of the specimen 2 on the image screen of the display unit 9. As a result, a surface analysis of a small area can be effected with a high degree of accuracy and reliability. Further, since the single focusing optical system 1 can be used for the two light sources, that is, the area locating light source 10 and the surface analyzing light source 11, also there is an advantage that the overall system can be made compact.

Figure 2:
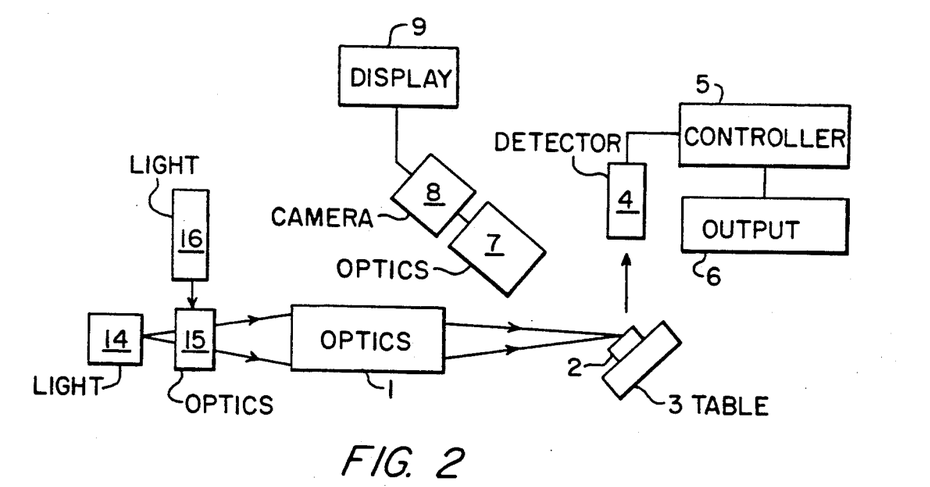
FIG. 2 shows another embodiment.

Embodiment 2:

FIG. 2 shows construction of a surface analyzing apparatus according to a second preferred embodiment of the present invention. Also the surface analyzing apparatus of the present embodiment employs a single focusing optical system 1 for two light sources. However, while in the first embodiment the positions of the area locating light source 10 and the surface analyzing light source 11 are moved or replaced upon setting and locating of an area and upon surface analysis of the area for the analysis, changing of the positions of the two light sources is not required in the present embodiment.

Referring to FIG. 2, the surface analyzing apparatus includes a surface analyzing light source 14, an area locating light source 16 and an optical system 15. The optical system 15 is designed such that it allows part or all of light of a wavelength ranging from a soft X-ray to a vacuum ultraviolet region from the surface analyzing light source 14 to pass or transmit therethrough while it introduces part or all of light from the area locating light source 16 to a focusing optical system 1 making use of reflection, passage, transmission or the like of light. When an area for the analysis is to be set and located, the area locating light source 16 is rendered operative and light from the light source 16 is introduced into the focusing light system 1 by way of the optical system 15, but when a surface analysis is to be effected for the small area thus set, the surface analyzing light source 14 is rendered operative and light from the light source 14 is introduced into the focusing optical system 1 by way of the optical system 15. When such optical system 15 is employed, there is no necessity of changing the positions of the two light sources 14 and 16 upon setting and locating of an area for the analysis and upon surface analysis. Functions, operations and effects of the other components of the surface analyzing apparatus are similar to those of the surface analyzing apparatus of the first embodiment described hereinabove.

With the surface analyzing apparatus of the present embodiment, since the optical system 15 is employed, setting and locating of an area for the analysis and a surface analysis for the thus set area for the analysis can be performed without the necessity of such changing or replacement of the positions of the surface analyzing light source 14 and the area locating light source 16 as described hereinabove in connection with the first embodiment. As a result, an analyzing operation can be performed rapidly comparing with the surface analyzing apparatus of the first embodiment.

Figure 3:
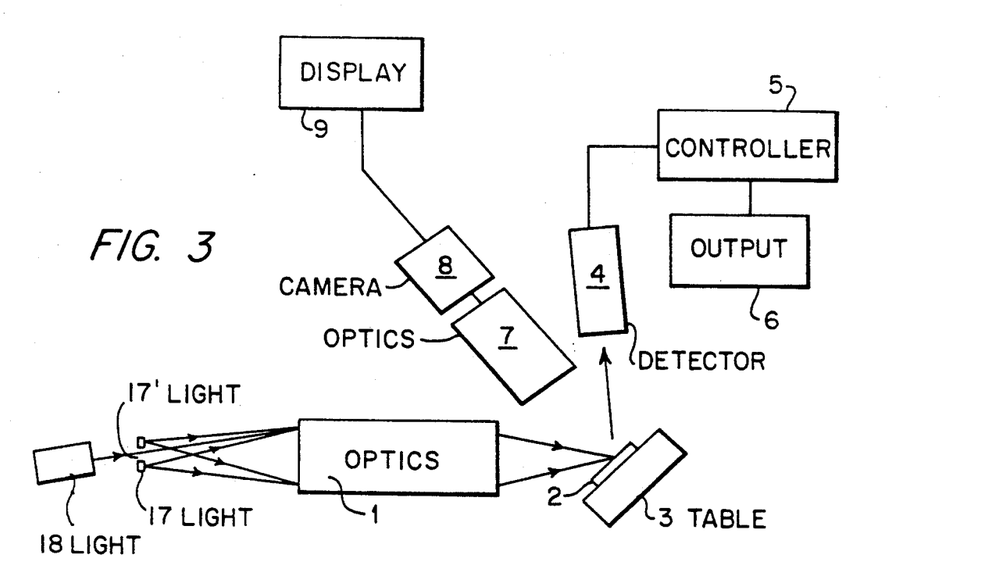
FIG. 3 shows another embodiment.

Embodiment 3:

FIG. 3 shows construction of a surface analyzing apparatus according to a third preferred embodiment of the present invention. The surface analyzing apparatus of the present embodiment is also constructed such that, similarly to the surface analyzing apparatus of the second embodiment described above, a surface analysis and setting and locating of an area for the analysis can be effected without the necessity of such changing of the positions of a surface analyzing light source and an area locating light source as described hereinabove in connection with the surface analyzing apparatus of the first embodiment.

Referring to FIG. 3, the surface analyzing apparatus shown includes a surface analyzing light source 17 and an area locating light source 18. The surface analyzing light source 17 has an aperture 17' through which light from the area locating light source 18 passes. Due to the construction, light from the two light sources 17 and 18 can be focused and irradiated upon a same position on a surface of a specimen 2 using a same optical system 1. Functions, operations and effects of the other components of the surface analyzing apparatus are similar to those of the surface analyzing apparatus of the first embodiment described hereinabove.

Also with the surface analyzing apparatus of the present embodiment, similar effects to those of the surface analyzing apparatus of the second embodiment can be achieved.

It is to be noted that, while in the foregoing description the surface analyzing light source 17 has the aperture 17' through which light from the area grasping light source 18 passes, the light sources 17 and 18 may play the opposite roles to each other. Further, while in the foregoing description the aperture 17' of the light source 17 is utilized to pass light from the light source 18 therethrough, the means for passing light from the light source 18 therethrough is not limited to such aperture 17', and some other means may be employed as such. For example, the light source 17 may be formed so thin that light from the light source 18 may pass therethrough. In short, the main point of the present embodiment resides in that all or part of light from the light source 18 passes or transmits through part of the light source 17, and any surface analyzing apparatus which employs such means is naturally included in the spirit and scope of the present invention.

Embodiment 4:

FIG. 4 shows construction of a surface analyzing apparatus according to a fourth preferred embodiment of the present invention. While in the first embodiment described hereinabove the optical system 1 and the specimen 2 are not moved but the light sources 10 and 11 are moved upon surface analysis and upon setting and locating of an area for the analysis, similar effects can be attained even if the light sources 10 and 11 are not moved but the optical system 1 and the specimen 2 are moved. The surface analyzing apparatus of the present invention is constructed to operate in such a manner just described.

Referring to FIG. 4, a focusing optical system 1 and a specimen table 3 are provided on a same moving mechanism 19, and a specimen 2 is placed on the specimen table 3. In FIG. 4, a condition of the surface analyzing apparatus upon locating of an area for the analysis is shown wherein an area locating light source 10 is located on an optical axis of the focusing optical system 1. After setting and locating of an area for the analysis is performed using the area locating light source 10, the optical system 1 and the specimen table 3 are moved using the moving mechanism 19 so that a surface analyzing light source 11 may now come to a position on the optical system of the focusing optical system 1. In this instance, the distances and the positional relationships between a surface of the specimen 2 and the detector 4 and between the surface of the specimen 2 and the optical system 7 are also changed. Consequently, the detector 4 and the optical system 7 are moved using moving mechanisms 20 and 21, respectively, so that the initial distances and positional relationships of the detector 4 and the optical system 7 from and with respect to the surface of the specimen 2 may be restored or maintained. The moving mechanisms 19, 20 and 21 are capable of providing precision movement on the order of microns, and moving operations of the moving mechanism 19, 20 and 21 are controlled using a controller 22. Functions, operations and effects of the other components of the surface analyzing apparatus are similar to those of the surface analyzing apparatus of the first embodiment described hereinabove.

Also with the surface analyzing apparatus of the present embodiment, similar effects to those of the surface analyzing apparatus of the first embodiment can be achieved.

Figure 5:
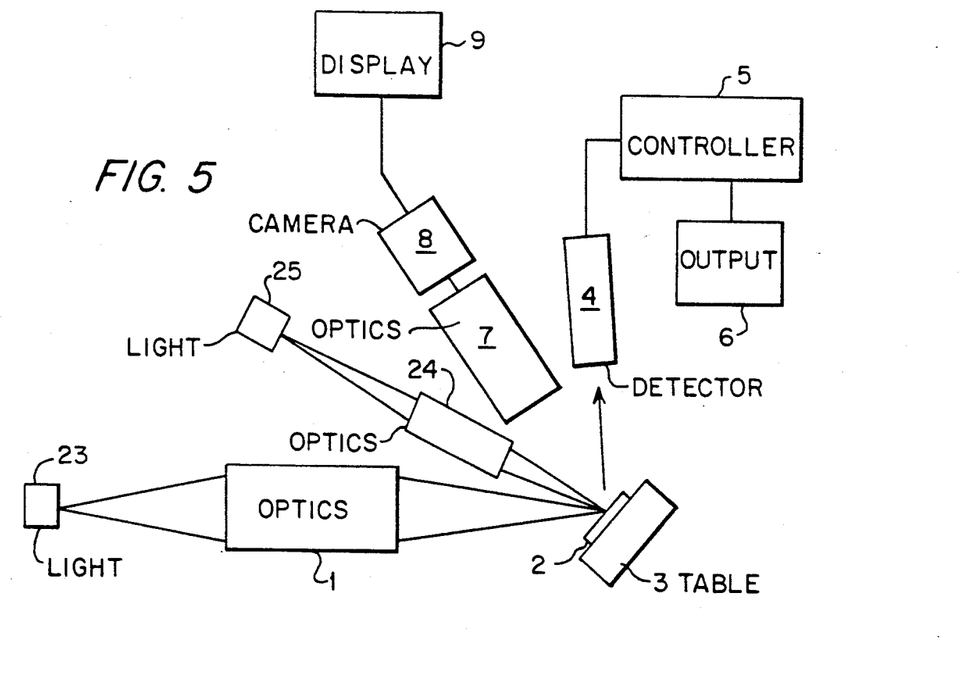
FIG. 5 shows another embodiment.

Embodiment 5:

FIG. 5 shows construction of a surface analyzing apparatus according to a fifth preferred embodiment of the present invention.

While in all of the surface analyzing apparatus of the preceding embodiments light for the surface analysis and light for the locating of an area for the analysis are both focused on a surface of a specimen using a common focusing optical system, similar effects can be attained with regard to setting and locating of an area for the analysis even if separate optical systems are used to focus light on a surface of a specimen. The surface analyzing apparatus of the present embodiment is constructed to operate in such a manner as just described.

Referring to FIG. 5, the surface analyzing apparatus includes a surface analyzing light source 23 for emitting light of a wavelength ranging from a soft X-ray to a vacuum ultraviolet radiation, and an area grasping light source 25 for emitting a visible radiation. Of optical systems for use for the focusing, an optical system 24 may be an arbitrary low aberration optical system while an optical system 1 is a reflecting type optical system. Light from the surface analyzing light source 23 is focused upon a surface of a specimen 2 using the optical system 1 while light from the area locating light source 25 is focused upon the surface of the specimen 2 using the optical system 24. In this instance, the optical systems 1 and 24 are adjusted in advance such that the positions of spots of focused light upon the surface of the specimen 2 may be a common position, or in other words, the centers of the spots of focused light may coincide with each other. Functions, operations and effects of the other components of the surface analyzing apparatus are similar to those of the surface analyzing apparatus of the first embodiment described hereinabove.

With the surface analyzing apparatus of the present embodiment, by focusing and irradiating light from the area locating light source 25 upon the surface of the specimen 2, setting and locating of an area for the analysis can be effected from the position of a spot of focused light.

Figure 6:
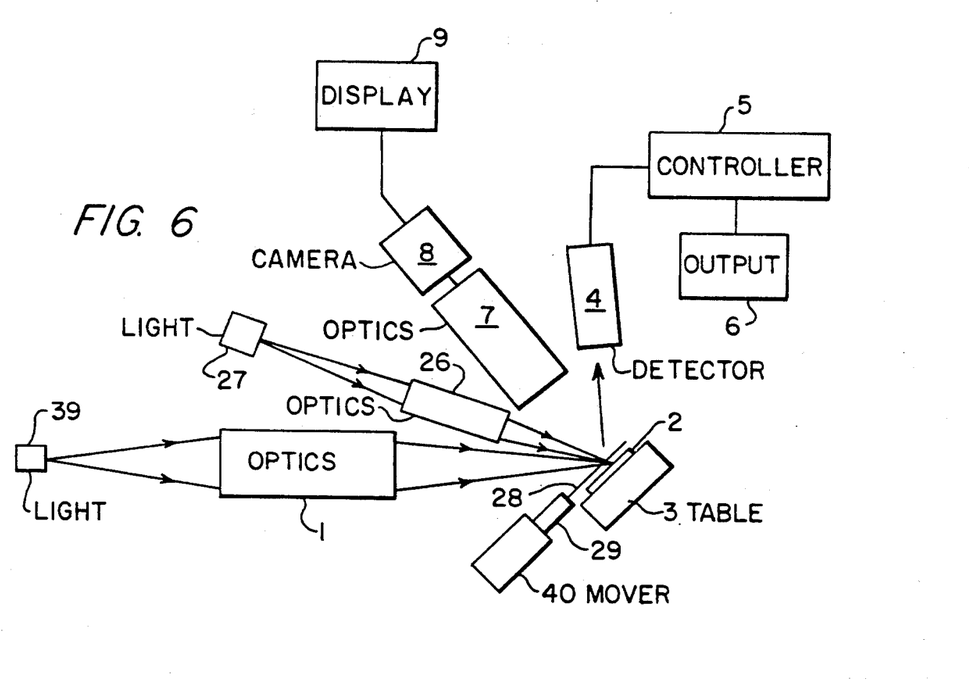
FIG. 6 shows another embodiment.

Embodiment 6:

FIG. 6 shows construction of a surface analyzing apparatus according to a sixth preferred embodiment of the present invention.

In the surface analyzing apparatus of the first to fifth embodiments described above, light for the setting and locating of an area for the analysis is a visible radiation, and it is a premise that a spot of focused light can be visually observed as it is. However, where an area for the analysis is very small, a spot of focused light for the setting and locating of an area for the analysis on a surface of a specimen 2 must be small correspondingly. Since the wavelength of light for the setting and locating of an area for the analysis must be substantially equal to or smaller than the diameter of a spot of focused light, when the diameter of a spot of focused light is such a small diameter as, for example, 0.01 micron, it is necessary to use, as a light source for the setting and locating of an area for the analysis, a source of light having a shorter wavelength than a visible radiation such as, for example, a vacuum ultraviolet light source. When such short wavelength light source is used, it is impossible to visually observe a spot of focused light on a surface of a specimen 2 as it is. The surface analyzing apparatus of the present embodiment is constructed so as to enable setting and locating of an area for the analysis even in such an instance.

Referring to FIG. 6, the surface analyzing apparatus shown includes a surface analyzing light source 39 and an area locating light source 27 for emitting light with a wavelength shorter than that of a visible radiation. Light from the surface analyzing light source 39 is focused upon a surface of a specimen 2 using an optical system 1 while light from the area locating light source 27 is focused upon the surface of the specimen 2 using an optical system 26. The optical systems 1 and 26 are adjusted in advance such that light therefrom may be focused at the same position on the surface of the specimen 2 similarly as in the surface analyzing apparatus of the fifth embodiment described above. As described above, a spot of focused light from the optical system 26 cannot be visually observed as it is. Thus, a visual observation plate 28 is used to allow visual observation. The visual observation plate 28 may be, for example, a thin plate having a fluorescent material deposited onto a surface thereof or a thin plate or film made of a raw material in which a fluorescent material is mixed. The visual observation plate 28 allows part or all of visible radiations to transmit therethrough. The visual observation plate 28 is mounted on a support table 29 and located just above a surface of a specimen 2. The position of the support table 29 is adjusted by a moving mechanism 40 so that the gap between the visual observation plate 28 and the surface of the specimen 2 may be smaller than 100 microns. Here, where the visual observation plate 28 is made sufficiently thin (less then 1 mm thick), a visible light image of the surface of the specimen 2 can be reflected on an image screen of a display unit 9 by way of the visual observation plate 28 (and the fluorescent material on or in the visual observation plate 28). Besides, since the fluorescent material is present on the surface or in the inside of the visual observation plate 28, a spot of focused light originating from light from the area locating light source 27 appears as a luminescent spot on the visual observation plate 28. Thus, located setting and locating of an area for the analysis can be effected by simultaneously observing the luminescent spot on the screen of the display unit 9 and an image of the surface of the specimen 2 similarly reflected on the screen of the display unit 9. When a surface analysis is to be effected after setting and locating of an area for the analysis, the visual observation plate 28 is moved to a position at which it does not interfere with a beam of light from the optical system 1 using the moving mechanism 40. Functions, operations and effects of the other components of the surface analyzing apparatus are similar to those of the surface analyzing apparatus of the first embodiment described hereinabove.

With the surface analyzing apparatus of the present embodiment, since the visual observation plate 28 is used, it is possible to use a source of light with a shorter wavelength than a visible light source as an area locating light source, and as a result, it is possible to set and locate a smaller area for the analysis.

It is to be noted that, strictly speaking, there is a little displacement between the luminescent spot on the visual observation plate 28 and the area for the analysis on the surface of the specimen 2. However, if the visual observation plate 28 is made sufficiently thin and the gap between the visual observation plate 28 and the surface of the specimen 2 is made sufficiently small, then the displacement can be reduced to such a level at which it will have no bad influence on a surface analysis.

The surface analyzing apparatus of the present embodiment is constituted such that setting and locating of an area for the analysis may be effected by observing a luminescent spot on the visual observation plate 28. The same analysis area setting and locating means as in the surface analyzing apparatus of the present invention can naturally be applied to any of the surface analyzing apparatus of the first to fifth embodiments shown in FIGS. 1 to 5.

Figure 7:
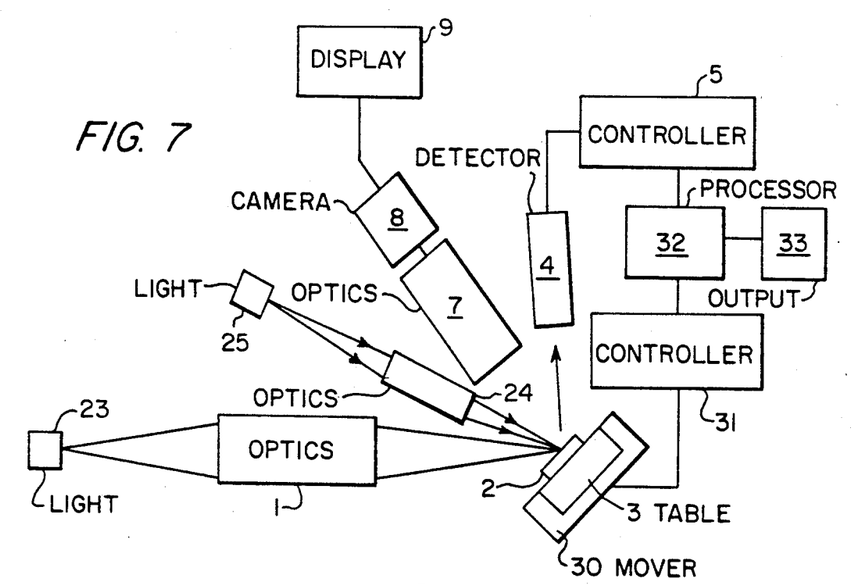
FIG. 7 shows another embodiment.

Embodiment 7:

FIG. 7 shows construction of a surface analyzing apparatus according to a seventh preferred embodiment of the present invention.

In any of the surface analyzing apparatus of the preceding embodiments described above, a beam of light for the surface analysis does not scan a surface of a specimen 2. However, if a beam of light for the surface analysis can be scanned on a surface of a specimen, then a result of analysis can be obtained as image information. In other words, distribution information can be obtained, and accordingly, a microscope for the observation of a chemical condition distribution or the like can be realized. Also in such an instance, means for determining a scanning area, that is, means for setting and locating an area for the analysis, is required. The surface analyzing apparatus of the present embodiment is constructed so as to meet such demand.

Referring to FIG. 7, focusing optical systems 1 and 24 are arranged in a similar manner as in the surface analyzing apparatus of the fifth embodiment shown in FIG. 5. Light from a light source 23 for the surface analysis is focused upon a surface of a specimen 2 using the optical system 1. Meanwhile, light from an area locating light source 25 is focused at the same position as the light from the light source 23 using the optical system 24. Thus, setting and locating of an area for the analysis can be effected on a reflected image on a display unit 9 by observing a spot of focused light originating from light from the area locating light source 25 on the surface of the specimen 2 using an optical system 7 and a camera 8.

In the meantime, a specimen table 3 on which the specimen 2 is placed is installed on a moving mechanism 30. The moving mechanism 30 is controlled by a controller 31 and is capable of providing high speed fine movement with a position tolerance smaller than 1 micron. A signal indicative of an amount of movement of the position of the moving mechanism 30, that is, indicative of an amount of movement of the position of the specimen 2, is transmitted from the controller 31 to a processing device 32. Meanwhile, a particle detection signal from a detector 4 is processed by a controller 5 and also inputted to the processing device 32. At the processing device 32, particle detection signals corresponding to various points on the surface of the specimen 2 are produced from the two signals, and if necessary, calculating processing is applied to the particle detection signals. Those results are inputted to an outputting/displaying device 33, and a result of the surface analysis is displayed as image information on the outputting/displaying device 33.

In the surface analyzing apparatus of the present embodiment, a specimen 2 is moved relative to beams of light for the surface analysis and for the setting and locating of an area for the analysis to cause the beams of light to scan the surface of the specimen 2. In this instance, the setting and locating of a scanning area on the surface of the specimen 2 can be effected making use of such scanning of the beam of light for the setting and locating of an area for the analysis.

With the surface analyzing apparatus of the present embodiment, it is possible to effect a surface analysis while setting and locating a scanning area of a beam of light for the surface analysis on a surface of a specimen 2. As a result, a distribution image of information regarding a chemical state can be obtained.

The surface analyzing apparatus of the present embodiment is an exemplary one of systems wherein two beams of light are scanned by the fine movement of a specimen 2, and such light beam scanning system can be applied to all of the apparatus which include any of the focusing means of the surface analyzing apparatus of the embodiments shown in FIGS. 1 to 6. All such applications are included in the spirit and scope of the present invention.

Figure 8:
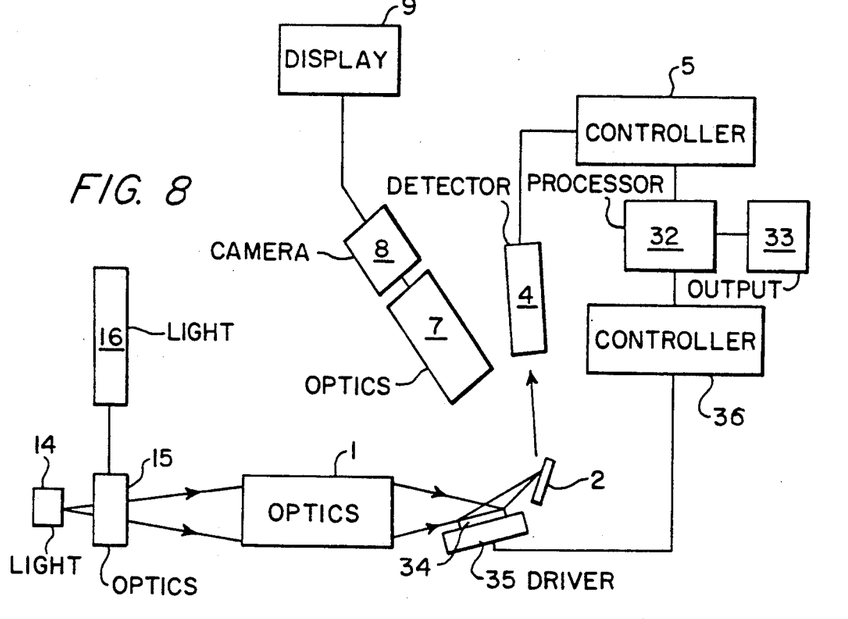
FIG. 8 shows another embodiment.

Embodiment 8:

FIG. 8 shows construction of a surface analyzing apparatus according to an eight preferred embodiment of the present invention which employs another scanning system for beams of light for the surface analysis and for the setting and locating of an area for the analysis. While in the surface analyzing apparatus of the seventh embodiment described above two beams of light are scanned by finely moving a specimen 2, in the surface analyzing apparatus of the present embodiment, two beams of light are scanned by using a reflecting mirror 34.

The surface analyzing apparatus of the present embodiment corresponds to the surface analyzing apparatus of the embodiment shown in FIG. 2 which additionally includes a beam scanning mechanism incorporated therein. Light from a surface analyzing light source 14 passes through an optical system 1 and is then reflected by a reflecting mirror 34 and focused upon a surface of a specimen 2. Also light from an area locating light source 16 is reflected similarly by the reflecting mirror 34 and then focused at the same position on the surface of the specimen 2 as the light from the surface analyzing light source 14. Accordingly, the setting and locating of an area for the analysis can be effected from a spot of focused light on the surface of the specimen 2 originating from the area locating light source 16.

Scanning of a beam of light for the surface analysis and another beam of light for the setting and locating of an area for the analysis on the surface of the specimen 2 is performed using the reflecting mirror 34 and a driving mechanism 35 for the reflecting mirror 34. In particular, the angle of the reflecting mirror 34 with respect to the optical axis of the optical system 1 is changed by the driving mechanism 35, and scanning of the two beams of light on the surface of the specimen 2 can be performed by continuously performing a changing operation of the angle. The driving mechanism 35 is controlled using a controller 36. A signal corresponding to an angle of the reflecting mirror 34 with respect to the optical axis of the optical system 1, that is, a signal corresponding to positions of the two beams of light on the surface of the specimen 2, is transmitted from the controller 36 to a processing device 32. The signal is used for the same object as a signal from the controller 31 of the surface analyzing apparatus of the seventh embodiment described above. Functions, operations and effects of the other components of the surface analyzing apparatus are similar to those of the surface analyzing apparatus of the second and seventh embodiments described hereinabove.

Also with the surface analyzing apparatus of the present embodiment, similar effects to those of the surface analyzing apparatus of the seventh embodiment described above can be attained. The present scanning system can be applied to apparatus which include any of the focusing means of the surface analyzing apparatus of the embodiments shown in FIGS. 1 to 3. All such applications are included in the spirit and scope of the present invention.

Figure 9:
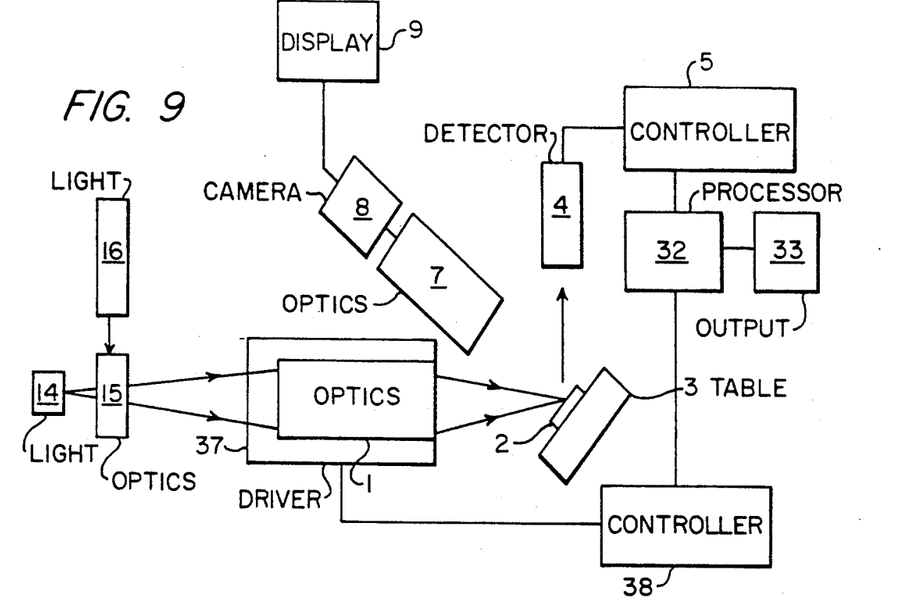
FIG. 9 shows another embodiment.

Embodiment 9:

FIG. 9 shows construction of a surface analyzing apparatus according to a ninth preferred embodiment of the present invention which employs a further scanning system for beams of light for the surface analysis and for the setting and locating of an area for the analysis. In the surface analyzing apparatus of the present embodiment, an optical system 1 is finely moved with respect to two beams of light to cause the two beams of light to scan.

Referring to FIG. 9, the optical system 1 is installed on a driving mechanism 37. The driving mechanism 37 is controlled using a controller 38 and is capable of providing high speed fine movement with a high degree of accuracy on the order of microns or less. By such fine movement of the optical system 1, a beam of light for the surface analysis and another beam of light for the setting and locating of an area for the analysis can be scanned on a surface of a specimen 2. Also in the surface analyzing apparatus of the present embodiment, a signal corresponding to positions of the two beams of light on the surface of the specimen 2 is transmitted from the controller 38 to a processing device 32 similarly as in the surface analyzing apparatus of the eighth embodiment described above. Functions, operations and effects of the other components of the surface analyzing apparatus are similar to those of the surface analyzing apparatus of the seventh and eighth embodiments described hereinabove.

Also with the surface analyzing apparatus of the present embodiment, similar effects to those of the seventh and eighth embodiments are obtained.

In the surface analyzing apparatus of the embodiments described above, a beam of light for the surface analysis is not necessarily required when an area for the analysis is to be set and located, and another beam of light for the setting and locating of an area for the analysis is not necessarily required when a surface analysis is to be effected. Accordingly, in any of the surface analyzing apparatus of the first to ninth embodiments (FIGS. 1 to 9), either one of such two beams of light may be cut by such means as, for example, turning off of power or an interrupter plate or the like which is used to prevent a beam of light from being irradiated upon a surface of a specimen.

Further, any apparatus which includes any suitable combination of the constructions of the surface analyzing apparatus of the first to ninth embodiments described above is naturally included in the spirit and scope of the present invention.

With the surface analyzing apparatus of the embodiments described above, it is possible to set and locate an area for the analysis and analyze a surface of a small area by focusing and irradiating a plurality of beams of light of wavelengths ranging from a soft X-ray to a vacuum ultraviolet region at a same position on a surface of a specimen, and as a result, a surface analysis can be effected with a high degree of accuracy and reliability.

Figure 10:
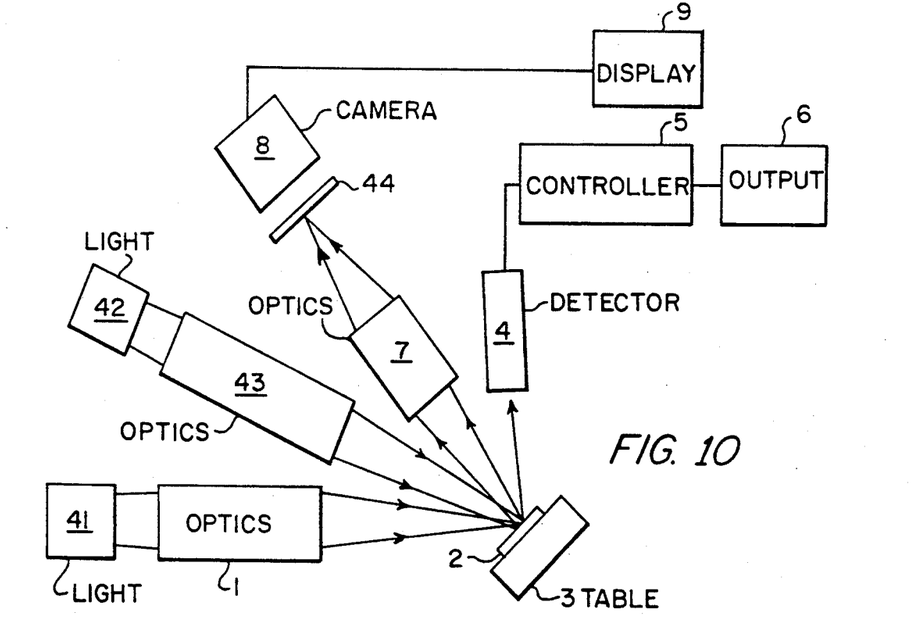
FIG. 10 shows another embodiment.

Embodiment 10:

FIG. 10 shows a surface analyzing apparatus according to a tenth preferred embodiment of the present invention. The surface analyzing apparatus shown includes a surface analyzing light source 41 for radiating light of a wavelength ranging from a soft X-ray to a vacuum ultraviolet region, and an area grasping light source 42 for radiating another light of a wavelength similarly ranging from a soft X-ray to a vacuum ultraviolet region. Light from the light source 41 having a wavelength ranging from a soft X-ray to a vacuum ultraviolet region is focused and irradiated upon a surface of a specimen 2 using a focusing optical system 1. Meanwhile, another beam of light from the light source 42 is irradiated over a range including and wider than the irradiation area of light from the optical system 1 using an optical system 43. In the light irradiation areas, electrons and fluorescent light are produced as a result of irradiation of the beams of light of wavelengths ranging from a soft X-ray to a vacuum ultraviolet region. The thus radiated electrons are analyzed in energy and detected by an electron detector 4 of the energy analyzing type. An electron detection signal is outputted as an observation signal to an outputting/displaying device 6 by way of a controller 5 for the detector 4. Meanwhile, the fluorescent light produced in the light irradiation areas is collected by an optical system 7 and projected in an enlarged scale on a fluorescent plate 44. Here, the optical system 7 observes all or part of the light irradiation area by the optical system 43. Since the efficiency in production of fluorescent light is different for elements which compose the surface of the specimen 2, an enlarged image of the light irradiation area by the optical system 43 is obtained on the fluorescent plate 44. The enlarged image is further enlarged by a camera 8 and reflected on a display unit 9. Since fluorescent light is produced intensely in the light irradiation area by the optical system 1 comparing with any other light irradiation area around the light irradiation area as described hereinabove, the light irradiation area by the optical system 1, that is, the area for the analysis, is observed as a particularly bright spot on the fluorescent plate 44 and hence on the display unit 9.

With the surface analyzing apparatus of the present embodiment, an area for the analysis can be confirmed readily on the display unit 9. Accordingly, elements and a chemical coupled condition in a small area can be identified with a high degree of accuracy.

Figure 11:
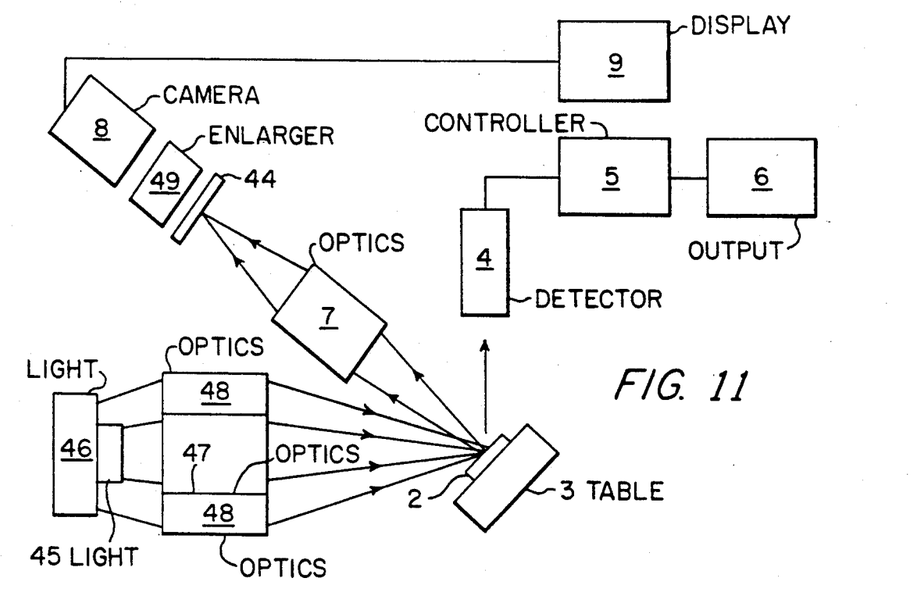
FIG. 11 shows another embodiment.

Embodiment 11:

If the focusing optical systems 1 and 43 in the surface analyzing apparatus of the tenth embodiment described above can be arranged in a coaxial relationship with each other, then the construction of the apparatus can be simplified and the size of the apparatus can be reduced, which is convenient in most cases. FIG. 11 shows a surface analyzing apparatus of an embodiment wherein focusing optical systems are arranged in a coaxial relationship with each other.

Referring to FIG. 11, the surface analyzing apparatus shown includes a surface analyzing light source 45 and an area locating light source 46. Focusing optical systems 47 and 48 are arranged in a coaxial relationship with each other. For example, a zone plate may be used as the optical system 47 while an optical system of the total reflection type such as, for example, an optical system of the Walter type, may be used as the optical system 48. In FIG. 11, the optical system 47 is shown as a focusing optical system for light for the surface analysis of a small area while the optical system 48 is shown as a focusing optical system for light for the locating of an area for the analysis. However, the optical systems 47 and 48 may otherwise play the opposite roles to each other. In this instance, the roles of the light sources 45 and 46 are also reversed. Fluorescent light produced as a result of irradiation of light from the optical systems 47 and 48 is focused by an optical system 7 and an image of the light irradiation area is obtained on a fluorescent plate 44 similarly as in the surface analyzing apparatus of the tenth embodiment described above. The image is further enlarged by an enlarging device 49 and reflected on a display unit 9 by way of a camera 8. Construction of the other components of the surface analyzing apparatus is similar to that of the surface analyzing apparatus of the tenth embodiment described hereinabove.

With the surface analyzing apparatus of the present embodiment, since the focusing optical system for light for the surface analysis of a small area and the focusing optical system for light for the locating of an area for the analysis are arranged in a coaxial relationship with each other, the size of the apparatus is reduced and the construction of the apparatus is simplified.

Embodiment 12:

For the confirmation of an area for the analysis, it is more convenient if the brightness of an image observed on a display unit 9 is variable. A surface analyzing apparatus of an embodiment of the present invention having such construction is shown in FIG. 12.

Figure 12:
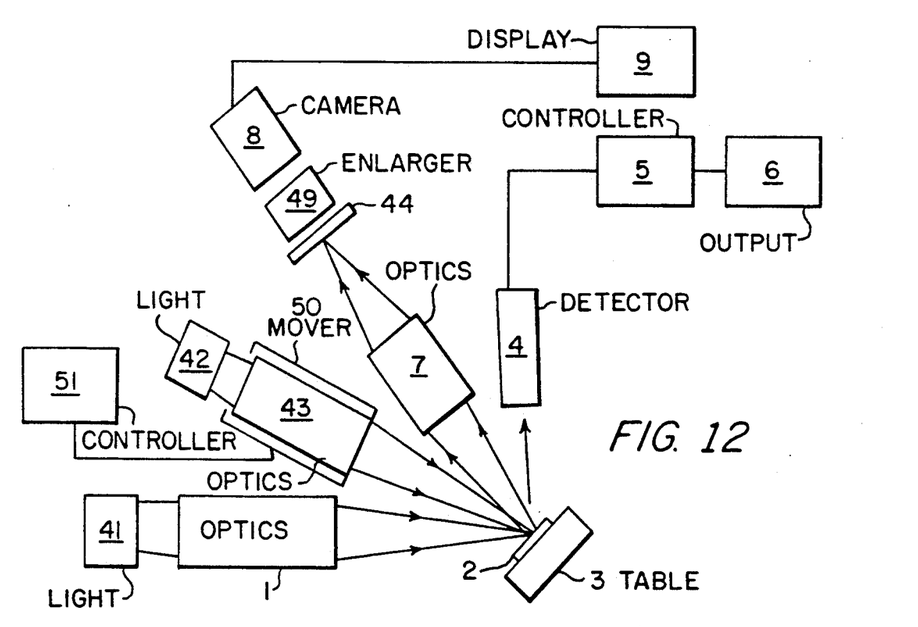
FIG. 12 shows another embodiment.

Referring to FIG. 12, the distance from an optical system 43 to a surface of a specimen 2 is variable. For the movement and fine adjustment of the optical system 43, a finely moving device 50 which is controlled by a controller 51 is used. By changing the distance between the optical system 43 and the surface of the specimen 2, the intensity of incident light to the surface of the specimen 2 is varied effectively, and the intensity of fluorescent light to be produced from a light irradiation area can be varied.

The method described above is one of many possible methods by which the brightness of an image is varied. In addition to the foregoing method, another method may be available wherein a filter or a mesh is interposed in a passage of light relating to the optical system 43. The surface analyzing apparatus is characterized in that the intensity or concentration of a beam of light for the locating of an area for the analysis is varied independently of the intensity of a beam of light for the surface analysis of a small area to change the contrast of an image to be observed on the display unit 9.

With the surface analyzing apparatus of the present embodiment, since the contrast of an image for the observation with respect to an area for the analysis can be varied, confirmation of the area for the analysis is further facilitated.

Figure 13:
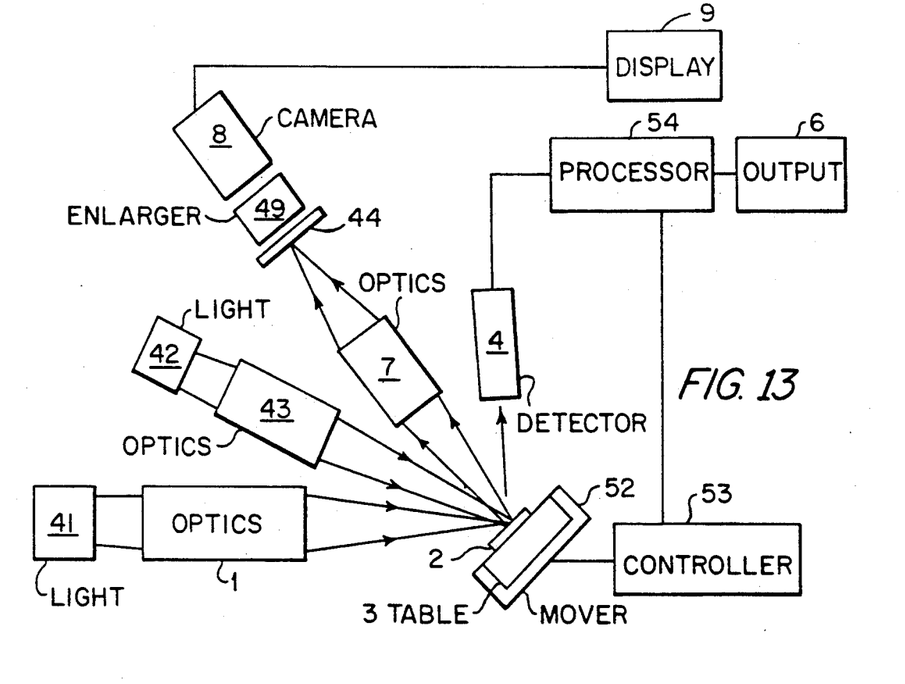
FIG. 13 shows another embodiment.

Embodiment 13:

FIG. 13 shows a surface analyzing apparatus of an embodiment wherein elements and a distribution of chemical coupled conditions on a surface of a specimen are identified. To find out such distribution in a particular area of a surface of a specimen is particularly important in analysis of residual contaminants on a surface of a semiconductor circuit element. Also in this instance, it must be identified which area of a surface of a circuit element is being analyzed.

Referring to FIG. 13, a specimen 2 is placed on a specimen table 3 which is in turn placed on a specimen moving mechanism 52. The specimen moving mechanism 52 is controlled by a controller 53 so that the specimen 2 may be moved finely. Such fine movement of the specimen 2 makes it possible for a beam of light to be scanned on a surface of the specimen 2. A signal regarding fine movement of the specimen 2 by the specimen moving mechanism 52 is transmitted from the controller 53 to a signal processing device 54. Meanwhile, also a detection signal from a detector 4 is inputted to the signal processing device 54. Data processing is executed on the signal processing device 54 in accordance with the signals thus received, and a result of such processing is transmitted to an outputting/displaying device 6.

With the surface analyzing apparatus of the present embodiment, elements and a distribution of chemical coupled conditions or the like on a surface of a specimen can be identified.

Figure 14:
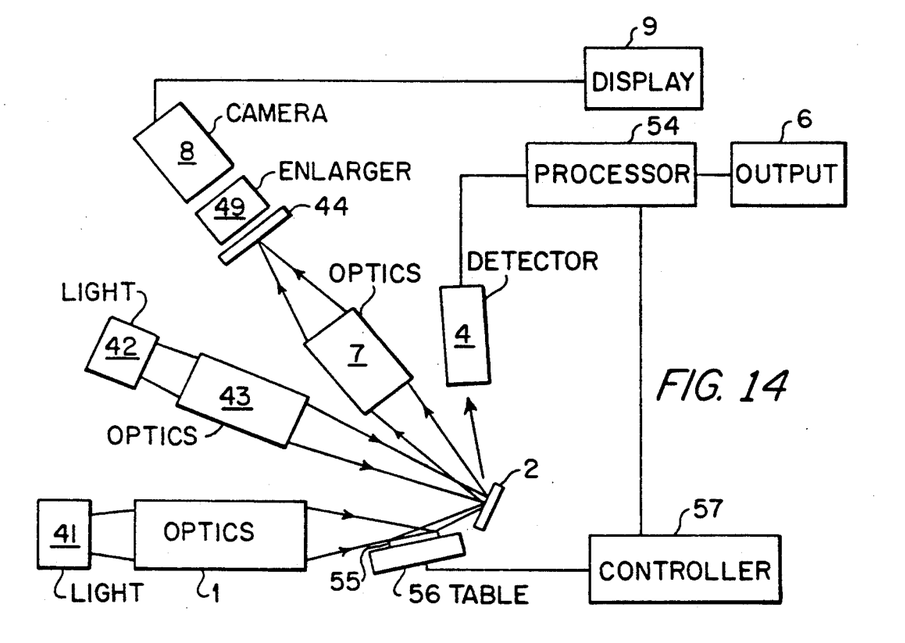
FIG. 14 shows another embodiment.

Embodiment 14:

FIG. 14 shows a surface analyzing apparatus of another embodiment wherein kinds of elements and a distribution of chemical coupled conditions or the like are identified.

In the surface analyzing apparatus shown in FIG. 14, a reflecting mirror 55 is interposed in a light passage from an optical system 1 to a specimen 2. The reflecting mirror 55 is located on a driving table 56 which is controlled by a controller 57 so that it may be pivoted by a small angle. Light focused by the optical system 1 is reflected by the reflecting mirror 55 and introduced to a surface of the specimen 2. Thereupon, the position of the incidence beam of light on the surface of the specimen 2 is varied by pivotal motion of the driving table 56 and hence the reflecting mirror 55 by a small angle, thereby causing the beam of light to scan the surface of the specimen 2.

Figure 15:
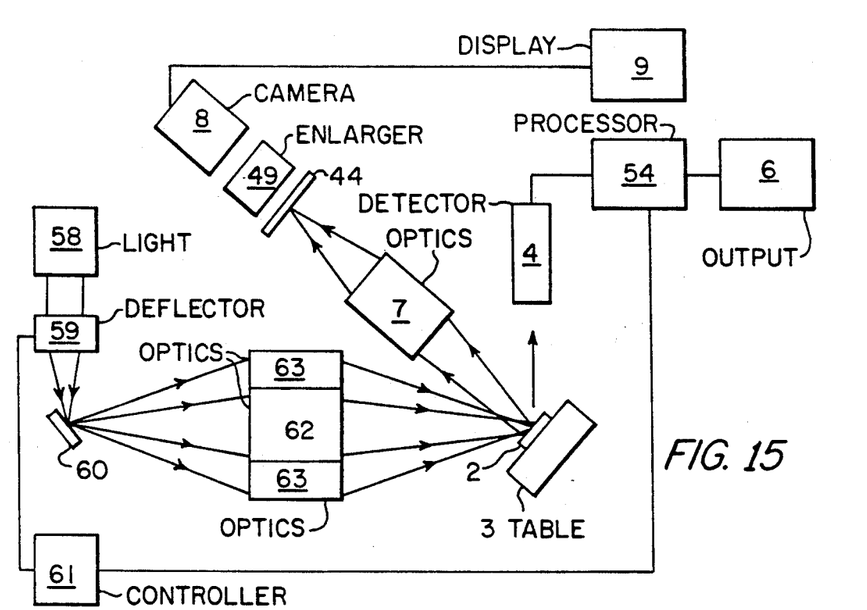
FIG. 15 shows another embodiment.

Embodiment 15:

FIG. 15 shows a surface analyzing apparatus of a further embodiment wherein kinds of elements and a distribution of chemical coupled conditions or the like are measured.

In the surface analyzing apparatus shown in FIG. 15, the position of a light source is varied to cause a beam of light from the light source to scan a surface of a specimen 2. A ray of charge particles from a charged particle source 58 is deflected by a deflecting system 59 and introduced to a target 60. As a result of such irradiation of the charged particle ray, light of a wavelength ranging from a soft X-ray to a vacuum ultraviolet region is produced in the irradiation area of the target 60. The light thus produced is focused by optical systems 62 and 63 and irradiated upon the surface of the specimen 2. Here, the optical system 62 is a focusing optical system for light for the locating of an area while the optical system 63 is another focusing optical system for light for the surface analysis. If the position on the target 60 from which light is produced is changed, then the irradiation position of light on the specimen 2 is changed. A signal corresponding to a change of the light producing position (and accordingly a change of the light irradiation position) is transmitted from a controller 61 to a signal processing device 54 at which it is processed together with a detection signal from a detector 4. Consequently, measurement of a distribution can be effected.

The surface analyzing apparatus of the present embodiment employs the optical systems 62 and 63 which are arranged in a coaxial relationship with each other. However, the scanning method in the surface analyzing apparatus of the present embodiment can be applied to an optical system which is not arranged in a coaxial relationship (for example, the optical system 1 shown in FIG. 10).

A method of locating an area for the analysis in distribution measurement has been described above with reference to FIGS. 13 to 15. Another method of causing a beam of light to scan a surface of a specimen may be available in addition to those methods described hereinabove. Any method which adopts such other methods shall be included in the spirit and scope of the present invention.

Embodiment 16:

Where light of a wavelength ranging from a soft X-ray to a vacuum ultraviolet region is employed as a beam of light for the locating of an area for the analysis, simultaneous irradiation of a beam of light for the surface analysis of a small area and another beam of light for the locating of an area for the analysis cannot be eliminated when an area for the analysis is to be located. However, when a surface analysis is to be effected for the area for the analysis after confirmation of the area for the analysis, a beam of light for the locating of an area for the analysis is sometimes unnecessary. A surface analyzing apparatus of an embodiment which copes with such case is shown in FIG. 16.

Figure 16:
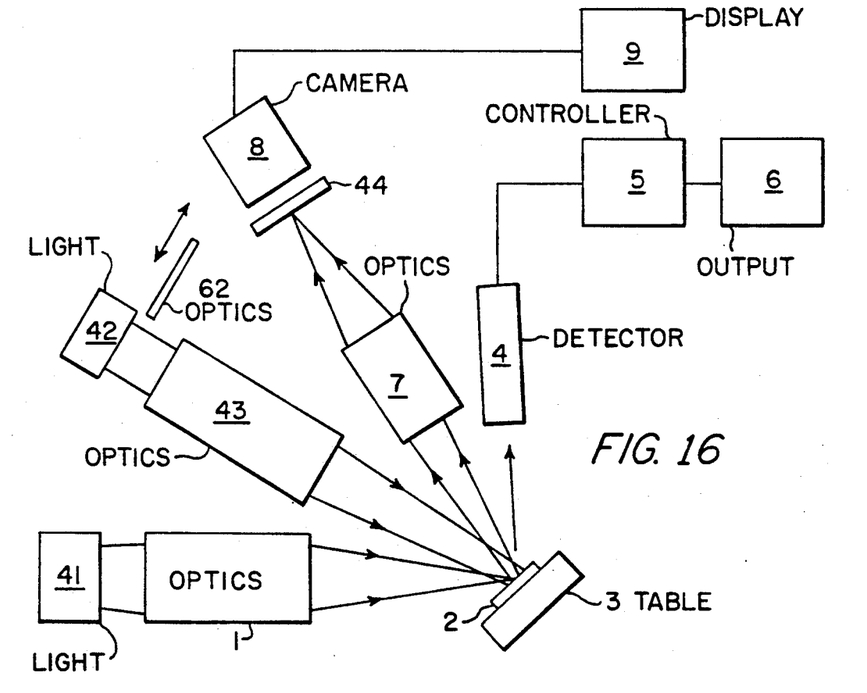
FIG. 16 shows another embodiment.

The surface analyzing apparatus of the embodiment shown in FIG. 16 corresponds to the surface analyzing apparatus of the embodiment shown in FIG. 10 in which a shutter 62a is additionally provided. By rendering the shutter 62 operative, irradiation of a beam of light unnecessary or inconvenient upon analysis of a small area can be removed. Naturally, such shutter mechanism can be incorporated in any of the surface analyzing apparatus of the embodiments shown in FIGS. 1 to 15.

With the surface analyzing apparatus of the present embodiment, since unnecessary or inconvenient irradiation of a beam of light can be removed upon analysis of a small area, locating of an area for the analysis can be effected readily, and besides the accuracy in analysis of a small area is improved.

Description has been given so far of various embodiments of the present invention. In any of the surface analyzing apparatus described above, the number of beams of light irradiated upon a surface of a specimen is two. However, only two beams of light may sometimes be insufficient to obtain a detection signal or fluorescent light of a predetermined intensity. In such an instance, three or more beams of light should be irradiated upon a surface of a specimen to increase the intensity of incident light to the surface of the specimen.

A method of using three or more beams of light more positively may also be available. Generally, the efficiency in production of fluorescent light is a function of energy of incident light. In case two or more beams of light having different wavelengths are considered as beams of light for the locating of an area for the analysis, when the intensity of fluorescent light originating from a beam of light having a certain wavelength is comparatively low, fluorescent light of an intensity sufficient for the observation of an enlarged image can be obtained by simultaneously irradiating another beam of light having another wavelength. Also in this instance, the irradiation area of a beam of light for the locating of an area for the analysis must necessarily include an irradiation area of a beam of light for the surface analysis of a small area.

In the surface analyzing apparatus of the embodiments described above, beam monitors, fine adjusting mechanisms for most of the optical systems and so forth are not shown in the drawings in order to make the natures of the individual embodiments clear. Such beam monitors and optical system fine adjusting mechanisms can be additionally incorporated in the surface analyzing apparatus of the individual embodiments if necessary. Further, any combination of the various elements described hereinabove in connection with the surface analyzing apparatus of the first to sixteenth embodiments or any combination of the surface analyzing apparatus of the individual embodiments shall be included in the spirit and scope of the present invention.

As apparent from the foregoing detailed description, according to the present invention, an area for the analysis can be set and located readily in surface analysis of a small area. As a result, identification or distribution measurement of kinds of elements, a chemical coupled condition and so forth in a small area or measurement can be performed with a higher degree of accuracy.

What is claimed is:

1. A surface analyzing method, comprising the steps of:

focusing a first beam of light having a wavelength ranging from a soft x-ray to a vacuum ultraviolet region into a thin first beam of light;

irradiating the thin first beam of light upon a surface of a specimen to cause emissions at an irradiation spot;

detecting physical information from the emissions to obtain analysis information of the surface of the specimen;

focusing a second different beam of light into a thin second beam of light;

irradiating the thin second beam of light over an area including and wider than the irradiation spot of the thin first beam of light upon the surface of the specimen;

obtaining an enlarged image of a spot of the thin second beam of light on the surface of the specimen by an enlarging optical system; and locating the position of the irradiation spot of the thin first beam of light on the surface of the specimen in accordance with the enlarged image.

2. A surface analyzing method according to claim 1, characterized in that the second beam of light is a beam of light having a wavelength in a visible light region.

3. A surface analyzing method according to claim 1, characterized in that the second beam of light is a beam of light having a wavelength in a wavelength region shorter than a visible light region.

4. A surface analyzing method according to claim 2, characterized in that the beam of light having a wavelength in a visible light region is a laser beam from a laser source.

5. A surface analyzing method according to any one of the preceding claims, characterized in that focusing of the first beam of light is effected using a focusing optical element which makes use of reflection of light.

6. A surface analyzing method according to any one of claims 1 to 4, characterized in that focusing of the second beam of light is effected using a focusing optical element which makes use of reflection of light.

7. A surface analyzing method according to any one of claims 1 to 4, characterized in that focusing of the first beam of light and focusing of the second beam of light are effected using a common focusing optical element.

8. A surface analyzing method, comprising the steps of:

focusing a first beam of light having a wavelength ranging from a soft x-ray to a vacuum ultraviolet region into a thin first beam of light;

irradiating the thin first beam of light upon a surface of a specimen to cause emissions at an irridiation spot;

detecting physical information from the emissions to obtain analysis information of the surface of the specimen;

focusing simultaneously with the irradiation of the first beam of light on the surface of the specimen, a second beam of light over an area including and wider than the irradiation spot of the first beam of light;

detecting fluorescent light produced from the surface of the specimen as a result of the irradiation of the first and second beams of light;

displaying an enlarged image of the surface of the specimen obtained by such detection of fluorescent light; and locating the position of the irradiation spot of the first beam of light on the surface of the specimen from a difference in contrast in the enlarged image.

9. A surface analyzing method according to claim 8, characterized in that the first beam of light is a monochromatic beam of light.

10. A surface analyzing method according to claim 9, characterized in that the second beam of light is a monochromatic beam of light.

11. A surface analyzing method according to claim 8, characterized in that the irradiation intensity of the second beam of light on the surface of the specimen is variable.

12. A surface analyzing method, comprising the steps of:

focusing a first beam of light having a wavelength ranging from a soft x-ray to a vacuum ultraviolet region into a thin first beam of light;

irradiating the thin first beam of light upon a surface of a specimen to cause emissions at an irradiation spot;

detecting physical information from the emissions to obtain analysis information of the surface of the specimen;

locating the irradiation spot of the first beam of light on the surface of the specimen by:

(i) focusing simultaneously with the irradiation of the first beam of light on the surface of the specimen, a second beam of light over an area including and wider than the irradiation spot of the first beam of light;

(ii) detecting fluorescent light produced from the surface of the specimen as a result of the irradiation of the first and second beams of light;

(iii) displaying an enlarged image of the surface of the specimen obtained by such detection of fluorescent light; and (iv) determining a position of the irradiation spot of the first beam of light on the surface of the specimen from a difference in contrast in the enlarged image; and said step of detecting physical information being characterized in that irradiation of the second beam of light on the surface of the specimen is not performed while a surface analysis by irradiation of the first beam of light is being performed.

13. A surface analyzing apparatus, comprising:

a first light source for producing a first beam of light having a wavelength ranging from a soft X-ray to a vacuum ultraviolet region;

first focusing means for focusing the first beam of light from said first light source into a thin beam of light and irradiating the first beam of light upon a surface of a specimen at an irradiation spot;

detecting means for detecting physical information obtained from an irradiation spot of the first beam of light on the surface of the specimen;

a second light source for producing a second beam of light having a different wavelength from that of the first beam of light;

second focusing means for focusing the second beam of light from the second light source into a thin beam of light and irradiating the second beam of light over an area including and wider than the irradiation spot of the first beam of light on the surface of the specimen; and means for observing the position of an irradiation spot of the second beam of light on the surface of the specimen.

14. A surface analyzing apparatus according to claim 13, characterized in that said second light source is a light source which produces a beam of light of a wavelength in a visible light region as the second beam of light.

15. A surface analyzing apparatus according to claim 13, characterized in that said second light source is a light source which produces a beam of light of a wavelength region shorter than a visible light region as the second beam of light.

16. A surface analyzing apparatus according to any one of claims 13 to 15, characterized in that said detecting means detects charged particles, photons or neutral particles radiated from the irradiation spot of the first beam of light.

17. A surface analyzing apparatus according to any one of claims 13 to 15, characterized in that said detecting means includes means for detecting energy of electrons or photons radiated from the irradiation spot of the first beam of light.

18. A surface analyzing apparatus according to any one of claims 13 and 14, characterized in that said second light source is a laser source which produces a laser beam of a wavelength in a visible light region as the second beam of light.

19. A surface analyzing apparatus according to any one of claims 13 to 15, characterized in that said first focusing means is constituted from a focusing optical system which makes use of reflection of light.

20. A surface analyzing apparatus according to claim 13, characterized in that said second focusing means is constituted from a focusing optical system which makes use of reflection of light.

21. A surface analyzing apparatus according to claim 13, characterized in that said first and second focusing means are constituted from a single focusing optical system.

22. A surface analyzing apparatus according to claim 21, characterized in that it further comprises light source moving means for alternately positioning said first and second light sources to a predetermined light source position with respect to said single focusing optical system.

23. A surface analyzing apparatus according to claim 21, characterized in that it further comprises means for introducing the first beam of light from said first light source and the second beam of light from said second light source simultaneously into said single focusing optical system.

24. A surface analyzing apparatus according to claim 13, characterized in that it further comprises scanning means for causing the positions of the irradiation spots of the first and second beams of light to two-dimensionally scan the surface of the specimen.

25. A surface analyzing apparatus according to claim 24, characterized in that said scanning means includes means for finely moving the specimen with respect to the first and second beams of light.

26. A surface analyzing apparatus according to claim 24, characterized in that said scanning means includes means for deflecting the first and second beams of light to scan the surface of the specimen.

27. A surface analyzing apparatus according to claim 26, characterized in that the deflecting scanning means includes a reflecting mirror for reflecting the first and second beams of light and introducing the same to the surface of the specimen, and a mechanism for changing the angles of said reflecting mirror with respect to the first and second beams of light.

28. A surface analyzing apparatus according to claim 24, characterized in that said scanning means includes means for finely moving a focusing optical system or systems which constitute said first and second focusing means.

29. A surface analyzing apparatus according to claim 15, characterized in that said means for observing the position of the irradiation spot of the second beam of light on the surface of the specimen includes a member in the form of a thin plate disposed proximate the surface of the specimen for receiving irradiation of the second beam of light and emitting fluorescent light therefrom.

30. A surface analyzing apparatus, comprising:
a first light source for producing a first beam of light having a wavelength ranging from a soft X-ray to a vacuum ultraviolet region;
first focusing means for focusing the first beam of light from said first light source into a thin beam of light and irradiating the first beam of light upon a surface of a specimen at an irradiation spot;
a second light light source for producing a second beam of light;
means for irradiating the second beam of light from said second light source over an area including and wider than the irradiation spot of the first beam of light; and
means for detecting fluorescent light emitted from the surface of the specimen as a result of the irradiation of the first and second beams of light and displaying an enlarged image of the surface of the specimen obtained by such detection of fluorescent light.

31. A surface analyzing apparatus according to claim 30, characterized in that said first light source produces a beam of monochromatic light.

32. A surface analyzing apparatus according to claim 30, characterized in that it further comprises monochromatic light forming means for changing the beam of light from said first light source into a beam of monochromatic light.

33. A surface analyzing apparatus according to claim 31 or 32, characterized in that said second light source produces a beam of monochromatic light.

34. A surface analyzing apparatus according to claim 31 or 32, characterized in that it further comprises monochromatic light forming means for changing the beam of light from said second light source into a beam of monochromatic light.

35. A surface analyzing apparatus according to claim 31 or 32, characterized in that the wavelength of the second beam of light is equal to the wavelength of the first beam of light.

36. A surface analyzing apparatus according to claim 30, characterized in that said detecting means detects electrons radiated from the irradiation spot of the first beam of light.

37. A surface analyzing apparatus according to claim 36, characterized in that said detecting means includes energy analyzing means for analyzing energy of electrons radiated from the irradiation spot of the first beam of light.

38. A surface analyzing apparatus according to claim 30, characterized in that it further comprises scanning means for causing the position of the irradiation spot of the first beam of light to two-dimensionally scan the surface of the specimen.

39. A surface analyzing apparatus according to claim 30, characterized in that it further comprises means for preventing irradiation of the second beam of light upon the surface of the specimen when said detecting means operates.

40. A surface analyzing apparatus according to claim 30, characterized in that it further comprises means for varying the irradiation intensity of the second beam of light upon the surface of the specimen.

* * * * *